US011428655B2

United States Patent
Matsukura et al.

(10) Patent No.: US 11,428,655 B2
(45) Date of Patent: Aug. 30, 2022

(54) GAS SENSOR

(71) Applicant: NGK SPARK PLUG CO., LTD., Nagoya (JP)

(72) Inventors: Yusuke Matsukura, Nagoya (JP); Shoji Kitanoya, Nagoya (JP); Masaya Watanabe, Nagoya (JP); Daisuke Ichikawa, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 407 days.

(21) Appl. No.: 16/749,348

(22) Filed: Jan. 22, 2020

(65) Prior Publication Data

US 2020/0249184 A1    Aug. 6, 2020

(30) Foreign Application Priority Data

Jan. 31, 2019 (JP) .............................. JP2019-015445

(51) Int. Cl.
*G01N 27/18* (2006.01)
*G01N 25/48* (2006.01)
*G01N 25/56* (2006.01)

(52) U.S. Cl.
CPC ....... *G01N 25/4893* (2013.01); *G01N 25/488* (2013.01); *G01N 25/56* (2013.01)

(58) Field of Classification Search
CPC combination set(s) only.
See application file for complete search history.

(56) References Cited

U.S. PATENT DOCUMENTS

| 2005/0042141 | A1* | 2/2005 | Otani | G01N 27/16 422/98 |
| 2015/0226688 | A1* | 8/2015 | Watanabe | G01N 27/18 73/31.05 |
| 2017/0284951 | A1* | 10/2017 | Pindl | H01L 23/3128 |
| 2019/0041347 | A1* | 2/2019 | Matsukura | G01N 27/4071 |
| 2020/0348252 | A1* | 11/2020 | Mueller | G01N 33/0027 |

FOREIGN PATENT DOCUMENTS

JP    2001-124716 A    5/2001

* cited by examiner

*Primary Examiner* — Lisa M Caputo
*Assistant Examiner* — Nasir U. Ahmed
(74) *Attorney, Agent, or Firm* — Sughrue Mion, PLLC

(57) ABSTRACT

A gas sensor (1) including a first gas detection element (2) and a second gas detection element (3), a first storage portion (4) having a first internal space (4A), and a first opening (4B) establishing communication between the first internal space (4A) and the outside space thereof exposed to a detection subject atmosphere, a second storage portion (5) having a second internal space (5A) and a second opening (5B) establishing communication between the second internal space (5A) and the outside space, a first membrane (4C) allowing permeation of water vapor and substantially not allowing permeation of a detection target gas, and covering the first opening (4B), and a calculation unit (12) for calculating the concentration of a detection target gas contained in the detection subject atmosphere, based on outputs from the first and second gas detection elements (2, 3), respectively.

3 Claims, 13 Drawing Sheets

GAS SENSOR

BACKGROUND OF THE INVENTION

1. Field of the Invention

The present invention relates to a gas sensor.

2. Description of the Related Art

A gas sensor is known for detecting an inflammable gas such as hydrogen or methane in which the influence of moisture (i.e., humidity) is suppressed (see Patent Document 1). In the gas sensor of Patent Document 1, a gas detection element is disposed in a first space open to a detection subject atmosphere (detection target gas), and a reference gas detection element is disposed in a second space having an opening that is covered with a membrane. The membrane allows water vapor contained in the detection subject atmosphere to permeate therethrough but not the detection target gas. Since the two gas detection elements are exposed to the same humidity condition, the gas sensor is considered to be able to detect the detection target gas without being influenced by humidity.

[Patent Document 1] Japanese Patent Application Laid-Open (kokai) No. 2001-124716

3. Problem to be Solved by the Invention

In a certain use environment of the above gas sensor, a large amount of water vapor is generated, resulting in a sharp increase in humidity. In the gas sensor, upon a large change in humidity of the detection subject atmosphere, the humidity in the space open to the detection subject atmosphere can immediately change in response to the humidity change of the detection subject atmosphere. In contrast, water vapor is introduced into the space whose opening is covered with the membrane, through the membrane. Accordingly, the humidity in the space whose opening is covered with the membrane does not immediately change in response to the humidity change of the detection subject atmosphere, but rather changes with a delay in response to the humidity change of the detection subject atmosphere. As a result, in some cases, a large difference in humidity (i.e., water vapor concentration) results between the two spaces in which the two gas detection elements are disposed respectively. In a period during which such a large humidity difference is present, the influence of water vapor detected by the gas detection element for detection must be taken into account. As a result, the gas sensor fails to properly measure the concentration of the detection target gas.

SUMMARY OF THE INVENTION

It is therefore an object of the invention to provide a gas sensor capable of accurately measuring the concentration of a detection target gas even in the event of a large change in the humidity of a detection subject atmosphere.

The above object has been achieved by providing (1) a gas sensor which comprises: paired first and second thermal conduction type gas detection elements; a first storage portion having a first internal space in which the first gas detection element is disposed, and having a first opening establishing communication between the first internal space and an outside space exposed to a detection subject atmosphere; a second storage portion having a second internal space in which the second gas detection element is disposed, and having a second opening establishing communication between the second internal space and the outside space; a first membrane formed of a material allowing permeation of water vapor and substantially not allowing permeation of a detection target gas, and disposed so as to cover the first opening; and a calculation unit for calculating a concentration of the detection target gas contained in the detection subject atmosphere introduced into the second internal space, based on outputs from the first gas detection element and the second gas detection element, respectively; wherein the gas sensor further comprises a second membrane formed of the same kind of material used to form the first membrane, having a thickness larger than that of the first membrane, and disposed so as to cover the second opening; the second membrane having a communication hole extending therethrough in a thickness direction for establishing communication between the outside space and the second internal space; and the gas sensor having a response time of 3 seconds or less for detecting the concentration of the detection target gas when the concentration of the detection target gas contained in the detection subject atmosphere is suddenly changed from 0 vol % to 2 vol % at a temperature of 25° C. in a state in which the detection subject atmosphere has a water vapor concentration of 2 vol %, and a water vapor concentration difference of 7 vol % or less is produced between the first internal space and the second internal space when the concentration of water vapor contained in the detection subject atmosphere is suddenly changed from 2 vol % to 18 vol % at a temperature of 60° C. in a state in which the detection subject atmosphere does not contain the detection target gas.

In a preferred embodiment (2) of the gas sensor (1), the detection target gas is hydrogen and the water vapor concentration difference between the first internal space and the second internal space is 6,300 ppm or less converted to hydrogen concentration. In a preferred embodiment (3) of the gas sensor (2), the water vapor concentration difference is calculated at the value of 6,300 ppm or less converted to hydrogen concentration by the calculation unit.

Effect of the Invention

The present invention can provide a gas sensor capable of accurately measuring the concentration of a detection target gas even in the event of a larger change in the humidity of a detection subject atmosphere.

DESCRIPTION OF REFERENCE NUMERALS

Figure 1:
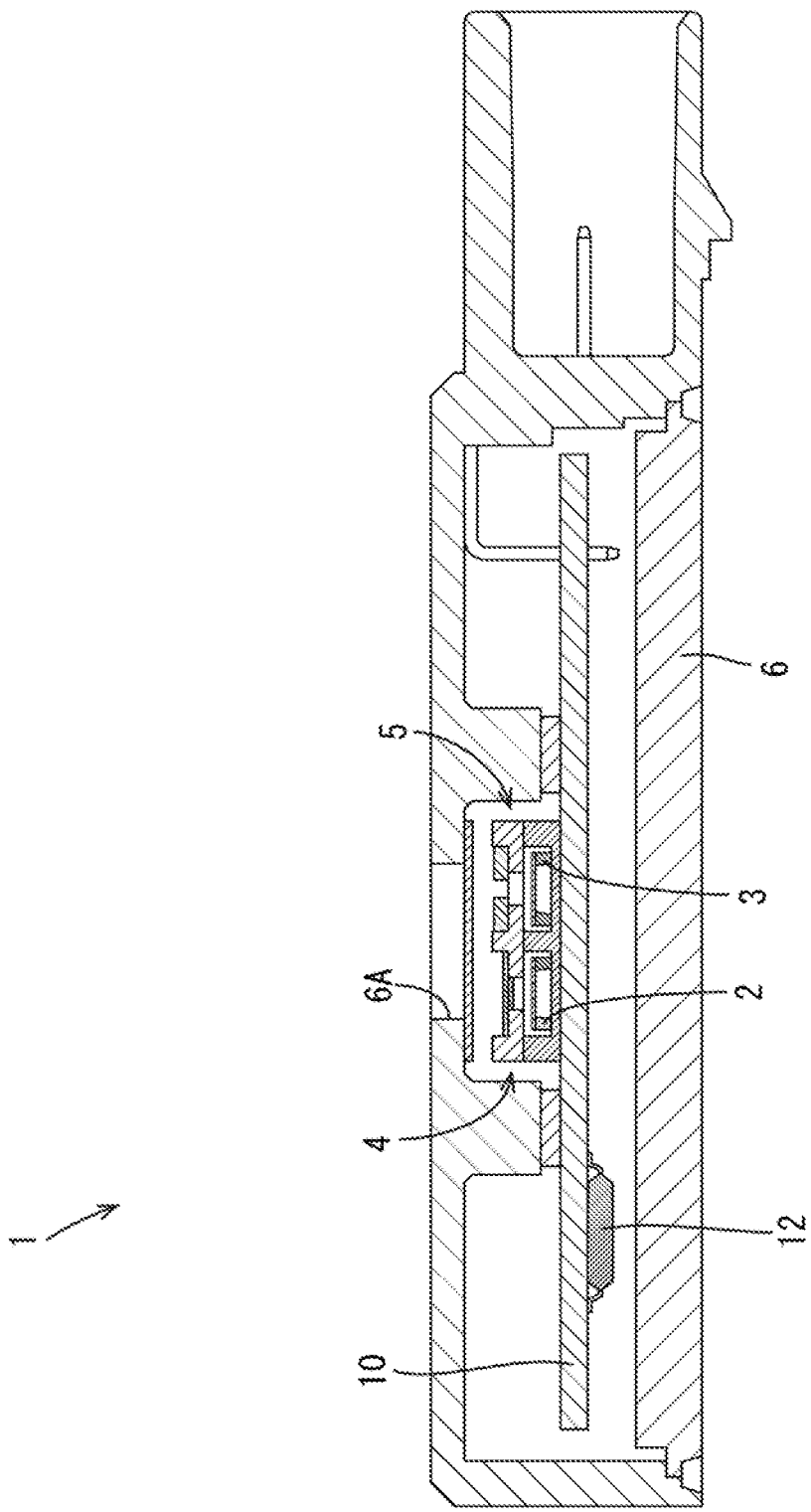
FIG. 1 is a sectional view schematically showing the structure of a gas sensor according to a first embodiment.

Reference numerals used to identify various features in the drawings include the following.

1: gas sensor; 2: first gas detection element; 3: second gas detection element; 4: first storage portion; 4A: first internal space; 4B: first opening; 4C: first membrane; 5: second storage portion; 5A: second internal space; 5B: second opening; 5C: second membrane; 5C1: communication hole; 6: casing; 7: pedestal; 8: protection cap; 10: circuit board; 11: seal member; and 12: calculation unit.

DETAILED DESCRIPTION OF THE PREFERRED EMBODIMENTS

The present invention will now be described in greater detail with reference to the drawings. However, the present invention should be construed as being limited thereto.

First Embodiment

Figure 2:
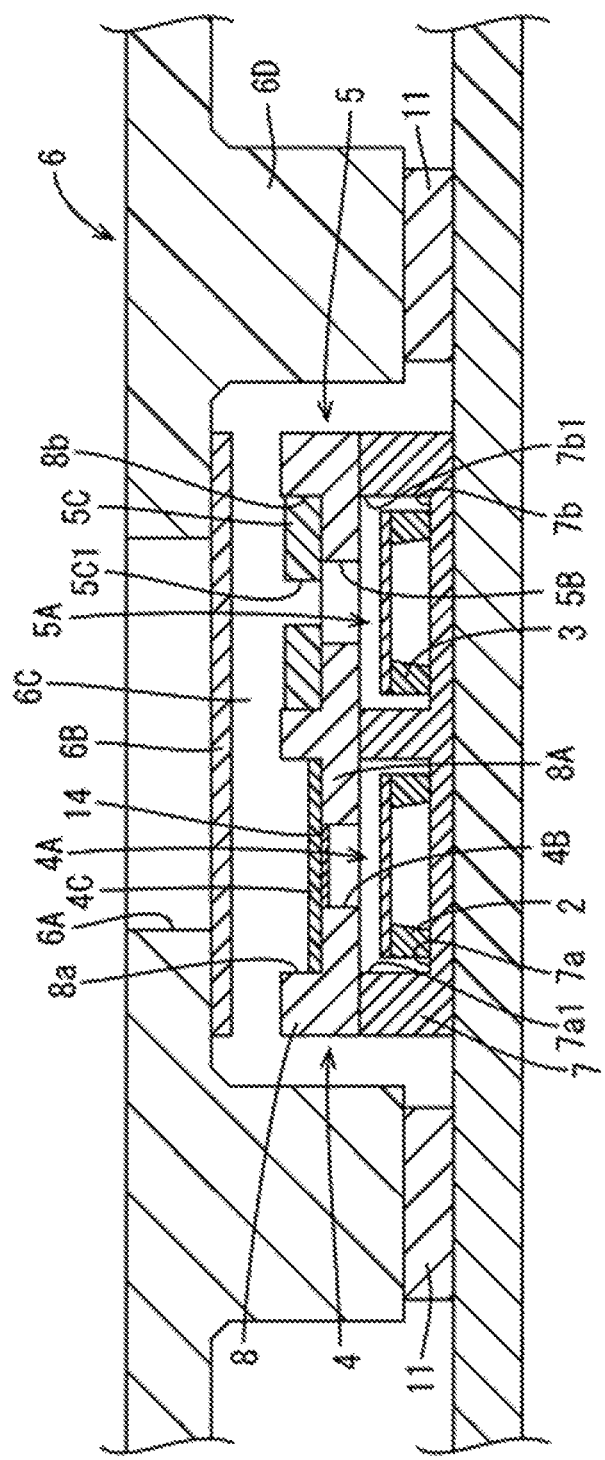
FIG. 2 is a fragmentary enlarged sectional view schematically showing the structure of a portion of the gas sensor, which portion includes a first storage portion, a second storage portion, and their vicinity.

A first embodiment of the present invention will next be described with reference to FIGS. 1 to 5. FIG. 1 is a sectional view schematically showing the structure of a gas sensor 1 according to the first embodiment, and FIG. 2 is a fragmentary enlarged sectional view schematically showing the structure of a portion of the gas sensor 1, which portion includes a first storage portion 4, a second storage portion 5, and their vicinity. The gas sensor 1 is a device for detecting hydrogen gas (detection target gas) contained in a detection subject atmosphere. As shown in FIGS. 1 and 2, the gas sensor 1 includes primarily a first gas detection element 2 and a second gas detection element 3, a first storage portion 4 and a second storage portion 5, a casing 6, a circuit board 10, and a calculation unit 12.

Figure 3:
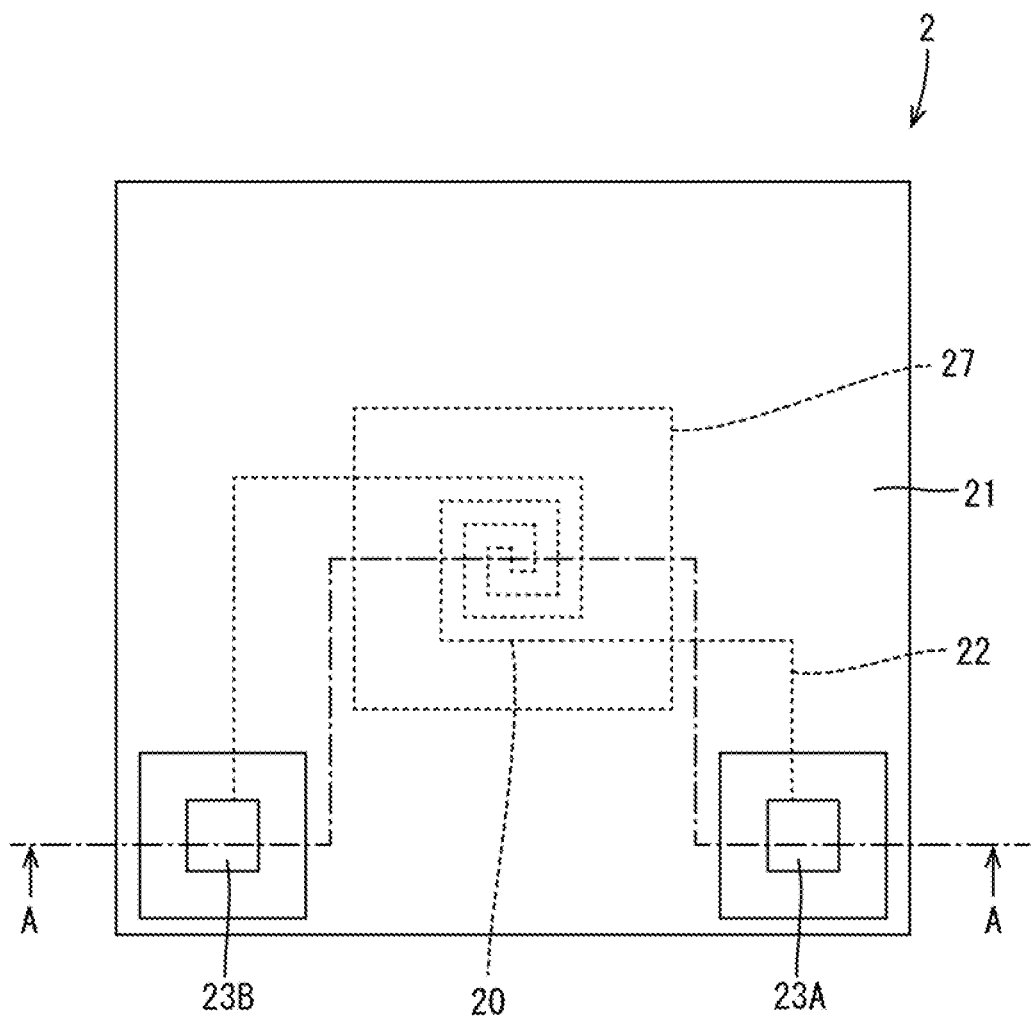
FIG. 3 is a plan view schematically showing the structure of a first gas detection element of the gas sensor.
Figure 4:
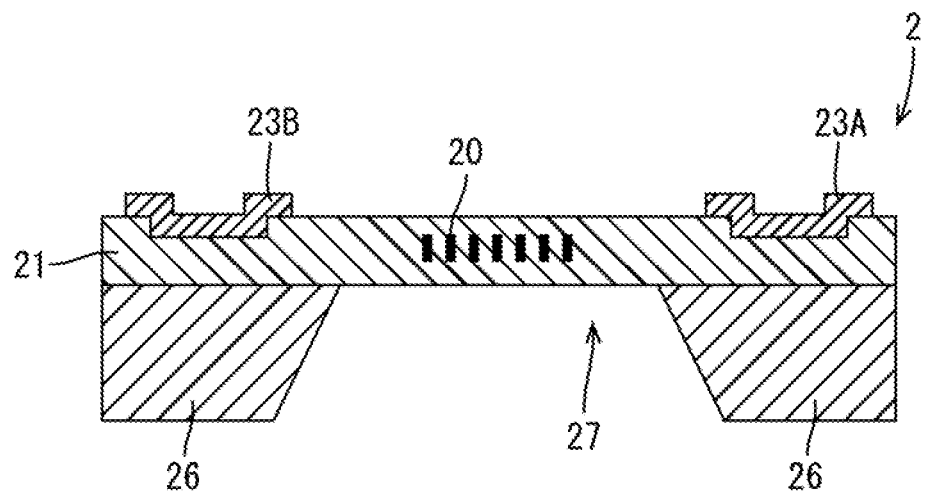
FIG. 4 is a sectional view taken along line A-A of FIG. 3.

The first gas detection element 2 is a thermal conduction type detection element having a heat-generating resistor whose resistance changes with the temperature of the resistor itself. The first gas detection element 2 serves as a detection element for reference use which is not exposed to a detection target gas. FIG. 3 is a plan view schematically showing the structure of the first gas detection element 2 of the gas sensor 1, and FIG. 4 is a sectional view taken along line A-A of FIG. 3. As shown in FIGS. 3 and 4, the first gas detection element 2 has a heat-generating resistor 20, an insulation layer 21, wiring 22, a pair of first electrode pads 23A and 23B, and a substrate 26.

The heat-generating resistor 20 is a conductor patterned in a spiral shape and is embedded in a central portion of the insulation layer 21. The heat-generating resistor 20 is electrically connected to the first electrode pads 23A and 23B through the wiring 22.

The first electrode pads 23A and 23B of the first gas detection element 2 are formed on the surface of the insulation layer 21. One of the first electrode pads 23A and 23B is connected to one of two second electrode pads (not shown) provided on the second gas detection element 3, described below. As shown in FIG. 4, the substrate 26 formed of silicon is laminated on a surface of the insulation layer 21 on a side opposite the first electrode pads 23A and 23B. The substrate 26 is absent in a region in which the heat-generating resistor 20 is disposed. This region assumes the form of a recess 27 in which the insulation layer 21 is exposed, thereby providing a diaphragm structure.

The heat-generating resistor 20 is a member whose resistance changes with the temperature of the resistor itself, and is formed of an electrically conductive material having a high temperature coefficient of resistance. For example, platinum (Pt) is used as the material for the heat-generating resistor 20.

The insulation layer 21 may be formed of a single material or may be composed of a plurality of layers of different materials. Examples of an electrically insulative material used to form the insulation layer 21 include silicon oxide ($SiO_2$) and silicon nitride ($Si_3N_4$).

Similar to the first gas detection element 2, the second gas detection element 3 is a thermal conduction type detection element having a heat-generating resistor 30 (see FIG. 5) whose resistance changes with the temperature of the resistor itself. The second gas detection element 3 is used as a detection element on a detection side which is exposed to the detection target gas and detects the detection target gas. Although unillustrated, similar to the first gas detection element 2, the second gas detection element 3 has the heat-generating resistor 30, an insulation layer, wiring, a pair of second electrode pads, and a substrate. One of the second electrode pads is connected to ground. Preferably, the heat-generating resistor 20 of the first gas detection element 2 and the heat-generating resistor 30 of the second gas detection element 3 (see FIG. 5) have the same resistance.

The first storage portion 4 is a box-shaped section which is composed of a pedestal 7 and a protection cap 8 and opens unidirectionally. The first storage portion 4 has a first internal space 4A in which the first gas detection element 2 is disposed, and a first opening 4B establishing communication between the first internal space 4A and a space outside the first storage portion 4 (an internal space 6C described below) exposed to a detection subject atmosphere. Similar to the first storage portion 4, the second storage portion 5 is a box-shaped section which is composed of the pedestal 7 and the protection cap 8 (described below) and opens unidirectionally. The second storage portion 5 has a second internal space 5A in which the second gas detection element 3 is disposed, and a second opening 5B establishing communication between the second internal space 5A and a space outside the second storage portion 5 (the internal space 6C described below) exposed to the detection subject atmosphere. The first storage portion 4 and the second storage portion 5 are formed by attaching the protection cap 8 to the pedestal 7 in a covering manner.

The pedestal 7 has a recess 7a having an opening 7a1 opening unidirectionally and in which the first gas detection element 2 is disposed, and a recess 7b having an opening 7b1 opening unidirectionally and in which the second gas detection element 3 is disposed. The two recesses 7a and 7b are disposed adjacent to each other. The pedestal 7 having such a structure is mounted on the surface of the circuit board 10. The pedestal 7 is formed of an insulating ceramic. Examples of a preferred insulating ceramic used to form the pedestal 7 include alumina, aluminum nitride, and zirconia. In the present embodiment, the pedestal 7 is formed of the same insulating ceramic as that used to form the protection cap 8.

The protection cap 8 is bonded to the pedestal 7 so as to cover the first gas detection element 2 and the second gas detection element 3 disposed in the two recesses 7a and 7b, respectively.

The protection cap 8 is formed of an insulating ceramic. An example of a preferred insulating ceramic used to form the protection cap 8 is alumina. As mentioned above, in the present embodiment, the pedestal 7 and the protection cap 8 are formed of the same insulating ceramic.

The pedestal 7 and the protection cap 8 are bonded together with an insulating adhesive. The insulating adhesive contains, as a main component, a thermosetting resin, a thermoplastic resin, an ultraviolet curing resin, or the like. In order to enhance adhesion between the pedestal 7 and the protection cap 8, an insulating adhesive which contains a thermosetting resin as a main component is preferred. A specific example of the thermosetting resin is an epoxy resin. Notably, the term "main component" as used herein means a component contained in the insulating adhesive in an amount of 80 mass % or more.

The protection cap 8 has the first opening 4B serving as an inlet/outlet of gas to/from the first storage portion 4, and the second opening 5B serving as an inlet/outlet of gas to/from the second storage portion 5. The protection cap 8 includes portions having a fixed thickness and has a body portion 8A applied over the opening 7a1 of the recess 7a and the opening 7b1 of the recess 7b. The first opening 4B and the second opening 5B extend through the body portion 8A in a thickness direction of the body portion 8A.

The first opening 4B extends between the outside and the inside (recess 7a side) of the first storage portion 4 while having the same size. Similar to the first opening 4B, the second opening 5B extends between the outside and the inside (recess 7b side) of the second storage portion 5 while having the same size. The first opening 4B and the second opening 5B have the same opening area.

In the present specification, the first internal space 4A of the first storage portion 4 consists of a space defined by the one recess 7a of the pedestal 7 and the body portion 8A of the protection cap 8, and a space connected to said space and located inside the first opening 4B. The second internal space 5A of the second storage portion 5 consists of a space defined by the other recess 7b of the pedestal 7 and the body portion 8A of the protection cap 8, and a space connected to said space and located inside the second opening 5B. In the present embodiment, the first internal space 4A and the second internal space 5A have the same size (volume).

As shown in FIG. 2, the first storage portion 4 and the second storage portion 5 are provided adjacent to each other while sharing one wall. The first internal space 4A in the first storage portion 4 and the second internal space 5A in the second storage portion 5 are proximate to each other. Accordingly, a temperature difference between the first internal space 4A and the second internal space 5A is reduced. As a result of having such a structure, the gas sensor 1 exhibits small output fluctuations caused by temperature changes, whereby an error in sensor output is suppressed.

A first membrane 4C is formed of material (solid polymer electrolyte) allowing permeation of water vapor and substantially not allowing permeation of the detection target gas (inflammable gas such as hydrogen gas or methane gas). Notably, in the present specification, the expression "substantially not allowing permeation" means that the amount of permeation of the detection target gas (hydrogen gas, etc.) is 1/50 or less of that of water vapor on a volume basis. As shown in FIG. 2, the first membrane 4C has a predetermined thickness (fixed thickness) and is fixed to the body portion 8A of the protection cap 8 so as to cover the entire first opening 4B using an adhesive or the like. The body portion 8A of the protection cap 8 has two recesses 8a and 8b formed therein and opening toward the outside (the internal space 6C described below), and the first membrane 4C is attached to the body portion 8A while being accommodated in the one recess 8a.

A fluororesin ion exchange membrane is preferably used as the first membrane 4C. Specific examples of the ion exchange membrane include Nafion®, Flemion®, and Aciplex®. Also, a hollow fiber membrane capable of separating the detection target gas and water vapor may be used as the first membrane 4C.

The first membrane 4C allows the permeation of water (water vapor) contained in the detection subject atmosphere present in the space outside the first storage portion 4 (the internal space 6C described below) toward the first internal space 4A. The first membrane 4C also allows the permeation of water (water vapor) present in the first internal space 4A toward the space outside the first storage portion 4.

Notably, the first membrane 4C in the present embodiment has a catalyst layer 14 laminated thereon for oxidizing the detection target gas (hydrogen gas, etc.). The catalyst layer 14 is laminated on the surface of the first membrane 4C located toward the first internal space 4A. Notably, the catalyst layer 14 allows the permeation of water vapor.

The second membrane 5C is formed of a material (solid polymer electrolyte) of the same type as that of the first membrane 4C. The thickness of the second membrane 5C is larger than that of the first membrane 4C. The second membrane 5C has a fixed thickness. A specific material of the second membrane 5C can be any one of the materials for the first membrane 4C exemplified above. Similar to the first membrane 4C, the second membrane 5C also allows the permeation of water vapor and substantially does not allow permeation of the detection target gas (inflammable gas such as hydrogen gas or methane gas).

The second membrane 5C also has a humidity-adjusting function of absorbing and releasing water (water vapor) in accordance with humidity. The larger the thickness of the second membrane 5C, the greater the effect (humidity-adjusting effect). Since the second membrane 5C is thicker than the first membrane 4C, the effect of the humidity-adjusting function is markedly increased.

As shown in FIG. 2, the second membrane 5C is fixed to the body portion 8A of the protection cap 8 so as to cover the entire second opening 5B using an adhesive or the like. The second membrane 5C is attached to the body portion 8A while being accommodated in the other recess 8b.

The second membrane 5C has a communication hole 5C1 extending therethrough in the thickness direction to establish communication between the second internal space 5A and the space outside the second storage portion 5 (the internal space 6C described below) exposed to the detection subject atmosphere. The second membrane 5C is attached to the body portion 8A of the protection cap 8 so that the communication hole 5C1 communicates with the second opening 5B. The size of the communication hole 5C1 is such that the second internal space 5A of the second storage portion 5 is visible from the outside, and allows direct introduction of the detection target gas and water vapor contained in the detection subject atmosphere into the second internal space 5A from the space outside the second storage portion 5. The communication hole 5C1 also allows discharge of the detection target gas and water vapor contained in the second internal space 5A to the space outside the second storage portion 5. In the present embodiment, the opening area of the communication hole 5C1 is smaller than that of the second opening 5B. The communication hole 5C1 in the present embodiment has a circular opening in plan view and has the same size along the thickness direction. The communication hole 5C1 is disposed at approximately the center of the second opening 5B in plan view. In plan view, a portion of the second opening 5B which does not overlap the communication hole 5C1 overlaps the second membrane 5C.

Notably, in the case of the second membrane 5C, water vapor is transmitted between the second internal space 5A and the space outside the second storage portion 5 by passing through the above-mentioned communication hole 5C1 and by permeating through the second membrane 5C. That is, the second membrane 5C allows water vapor present in the space outside the second storage portion 5 to permeate toward the second internal space 5A and allows water vapor present in the second internal space 5A to permeate toward the space outside the second storage portion 5.

The casing 6 accommodates the first storage portion 4 and the second storage portion 5. The casing 6 has an opening 6A for introducing therein the detection subject atmosphere which contains the detection target gas, and a filter 6B disposed over the underside of the opening 6A.

Specifically, the first storage portion 4 and the second storage portion 5 (i.e., the pedestal 7 and the protection cap 8) are accommodated in the internal space 6C provided between the casing 6 and the circuit board 10. The internal space 6C is formed by fixing the circuit board 10 to an internally protruding inner frame 6D of the casing 6 through a seal member 11. That is, the internal space 6C is surrounded by the casing 6, the circuit board 10, and the seal member 11 used to fix the casing 6 and the circuit board 10 together.

The opening 6A is formed so as to establish communication between the detection subject atmosphere and the internal space 6C. That is, the space outside the first storage portion 4 and the second storage portion 5 is exposed to the detection subject atmosphere. The detection subject atmosphere introduced into the internal space 6C through the opening 6A is supplied to both the first internal space 4A and the second internal space 5A.

The filter 6B is a water repellent filter which allows the detection target gas or the like to permeate therethrough and which does not allow liquid water to permeate therethrough (i.e., the filler removes water droplets contained in the detection target gas). The filter 6B restrains entry of water droplets and other foreign matter into the internal space 6C through the opening 6A. In the present embodiment, the filter 6B is attached to the inner surface of the casing 6 so as to cover the opening 6A.

Figure 5:
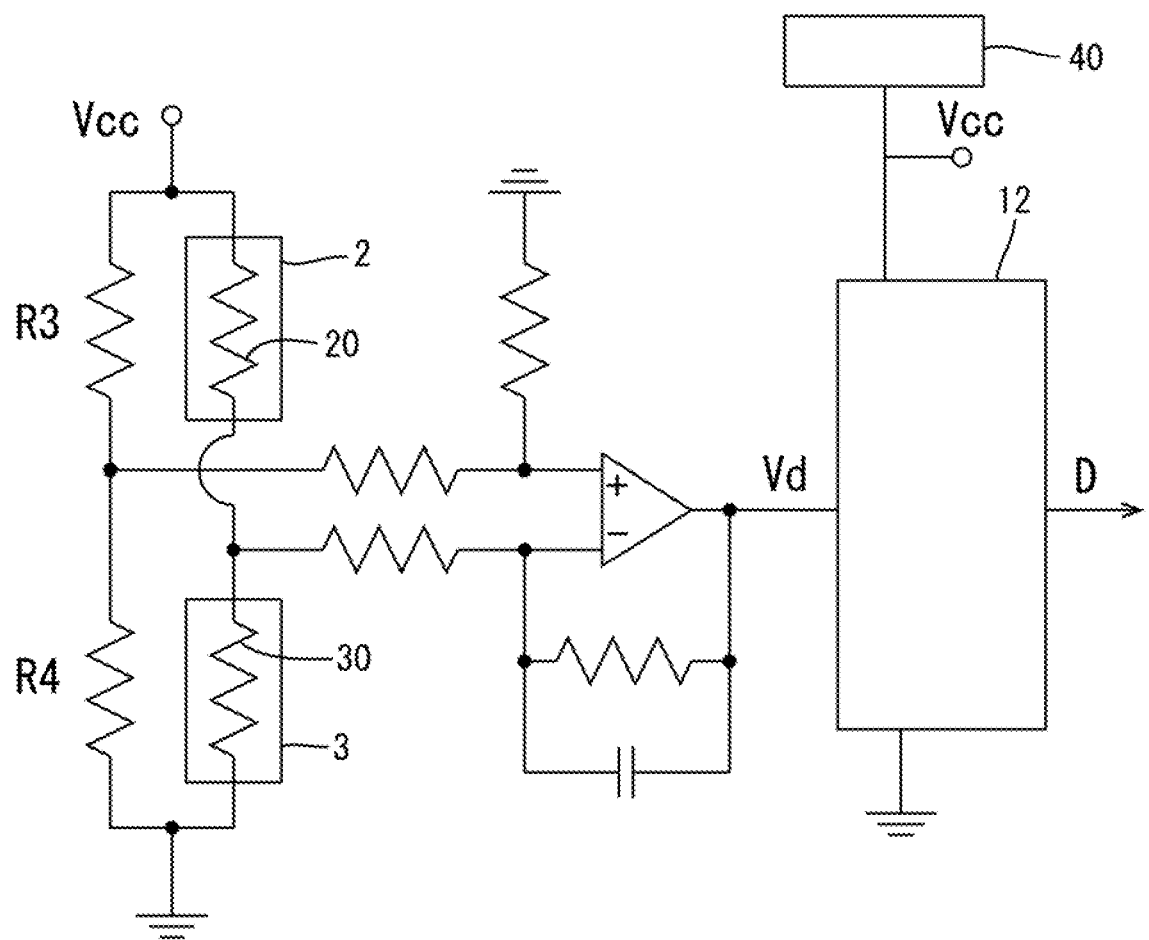
FIG. 5 is a schematic circuit diagram of the gas sensor.

FIG. 5 is a schematic circuit diagram of the gas sensor 1. The circuit board 10 is a plate-shaped board disposed within the casing 6 and has the circuit shown in FIG. 5. The circuit is electrically connected to the first electrode pads 23A and 23B of the first gas detection element 2 and to the first electrode pads of the second gas detection element 3.

The calculation unit 12 calculates the concentration of the detection target gas contained in the detection subject atmosphere introduced into the second internal space 5A, based on the outputs from the first gas detection element 2 and the second gas detection element 3. Specifically, as shown in FIG. 5, the calculation unit 12 calculates the concentration from an electric potential present between the heat-generating resistor 20 of the first gas detection element 2 and the heat-generating resistor 30 of the second gas detection element 3 when a constant voltage Vcc is applied to the heat-generating resistor 20 of the first gas detection element 2 and the heat-generating resistor 30 of the second gas detection element 3 connected in series.

More specifically, the calculation unit 12 obtains an electric potential difference Vd output from an operation amplifier circuit which amplifies (i) an electric potential difference between an electric potential at a point between the heat-generating resistor 20 of the first gas detection element 2 and the heat-generating resistor 30 of the second gas detection element 3, and (ii) an electric potential at a point between a fixed resistance R3 and a fixed resistance R4 disposed in parallel with the heat-generating resistors 20 and 30. The calculation unit 12 calculates the concentration D of the detection target gas (hydrogen gas) from the electric potential difference Vd and outputs the concentration D.

A DC power source 40 supplies current to the calculation unit 12 and the circuit board 10. The DC power source 40 applies voltage to the heat-generating resistor 20 of the first gas detection element 2 and to the heat-generating resistor 30 of the second gas detection element 3.

The gas sensor 1 of the present embodiment is set such that its response time for the detection target gas becomes 3 seconds or less in the detection target gas response test. In the detection target gas response test, the response time Y (sec) of the gas sensor 1 for the detection target gas is measured by suddenly changing the concentration of the detection target gas (e.g., the concentration of hydrogen) contained in the detection subject atmosphere from 0 vol % to 2 vol % at a temperature of 25° C. in a state in which the detection subject atmosphere has a water vapor concentration of 2 vol %. In the gas sensor 1, for example, the size (particularly, opening area) of the communication hole 5C1 of the second membrane 5C, etc., are adjusted as appropriate such that the response time Y (sec) becomes 3 seconds or less. The detection target gas response test will be described in detail below.

The gas sensor 1 is also set such that the difference in water vapor concentration (maximum water vapor concentration difference X) between the first internal space 4A and the second internal space 5A becomes equal to or less than 7 vol % in a humidity transition test. In the humidity transition test, the difference in water vapor concentration between the first internal space 4A and the second internal space 5A is measured by suddenly changing the concentration of water vapor contained in the detection subject atmosphere from 2 vol % to 18 vol % at a temperature of 60° C. in a state in which the detection subject atmosphere does not contain the detection target gas (e.g., hydrogen gas). In the gas sensor 1, for example, the thickness of the second membrane 5C, the size (particularly, opening area) of the communication hole 5C1 of the second membrane 5C, the thickness of the first membrane 4C, etc., are adjusted as appropriate such that the difference in water vapor concentration (maximum water vapor concentration difference X) between the first internal space 4A and the second internal space 5A becomes 7 vol % or less. The humidity transition test is described in detail below.

In the case where the detection target gas is hydrogen, in the humidity transition test, preferably, the difference in water vapor concentration between the first internal space 4A and the second internal space 5A is 6,300 ppm or less converted to hydrogen concentration. The value converted to hydrogen concentration is a value output by the calculation unit 12 when it calculates the water vapor concentration difference.

The thus-configured gas sensor 1 of the present embodiment can accurately measure the detection target gas concentration (hydrogen gas concentration, etc.) even when the humidity of the detection subject atmosphere changes greatly from a low level to a high level as a result of, for example, generation of a large amount of water vapor around the gas sensor 1. The principle of this function will be described below.

In the event of a large change in the water vapor concentration of the detection subject atmosphere from a low level to a high level (e.g., a change in the water vapor concentration of the detection subject atmosphere from 2 vol % to 18 vol % at a temperature of 60° C.), water vapor contained in the detection subject atmosphere present in the space outside the first storage portion 4 permeates through the first membrane 4C and also passes through the first opening 4B to thereby enter the first internal space 4A of the first storage portion 4. The first storage portion 4 accommodates the first gas sensor element 2 for reference use. As a result, the water vapor concentration of the first internal space 4A increases as compared with its condition before entry of water vapor. On the other hand, the detection target gas contained in the target subject atmosphere substantially fails to permeate through the first membrane 4C and is thus restrained from entering the first internal space 4A.

In the above-mentioned event of a larger change in the water vapor concentration of the detection subject atmosphere from a low level to a high level, water vapor contained in the detection subject atmosphere present in the space outside the second storage portion 5 passes mainly through the communication hole 5C1 of the second membrane 5C and through the second opening 5B to thereby directly enter the second internal space 5A of the second storage portion 5. The internal space 5A accommodates the second gas detection element 3 for detection use. The amount of water vapor passing through the communication hole 5C1 is expected to be large as compared with the amount of water vapor permeating through the first membrane 4C. However, as mentioned above, since the second membrane 5C in the present embodiment has a humidity-adjusting function which varies according to the thickness thereof, water vapor or the like introduced into the second internal space 5A is adjusted appropriately through absorption, etc., by the second membrane 5C. Consequently, the water vapor concentration of the second internal space 5A does not become excessively high as compared with that of the first internal space 4A. On the other hand, the detection target gas contained in the detection subject atmosphere passes through the communication hole 5C1 of the second membrane 5C and through the second opening 5B to thereby directly enter the second internal space 5A.

As mentioned above, the gas sensor 1 of the present embodiment can accurately measure the detection target gas concentration (hydrogen gas concentration, etc.) even when the humidity of the detection subject atmosphere changes greatly from a low level to a high level as a result of, for example, generation of a large amount of water vapor around the gas sensor 1. Also, the gas sensor 1 of the present embodiment can accurately measure the detection target gas concentration (hydrogen gas concentration, etc.) even when the humidity of the detection subject atmosphere changes greatly from a high to a low level.

The gas sensor 1 of the present embodiment is disposed for use, for example, within the engine compartment (behind the hood) of an automobile.

Next, the detection target gas response test will be described with reference to FIGS. 6 to 8. In the detection target gas response test, the response time Y of the gas sensor 1 for the detection target gas is measured by suddenly changing the concentration of the detection target gas (e.g., the concentration of hydrogen) contained in the detection subject atmosphere from 0 vol % to 2 vol % at a temperature of 25° C. in a state in which the detection subject atmosphere has a water vapor concentration of 2 vol %. The detection target gas response test uses the gas sensor 1 in which the opening area of the first opening 4B on the reference side and the opening area of the second opening 5B on the detection side are set to 3.4 mm$^2$ (1.7 mm×2.0 mm). Further, the volume of the first internal space 4A on the reference side and the volume of the second internal space 5A on the detection side are set to 8.1 mm$^3$. A detailed description of the test method is given below.

Figure 6:
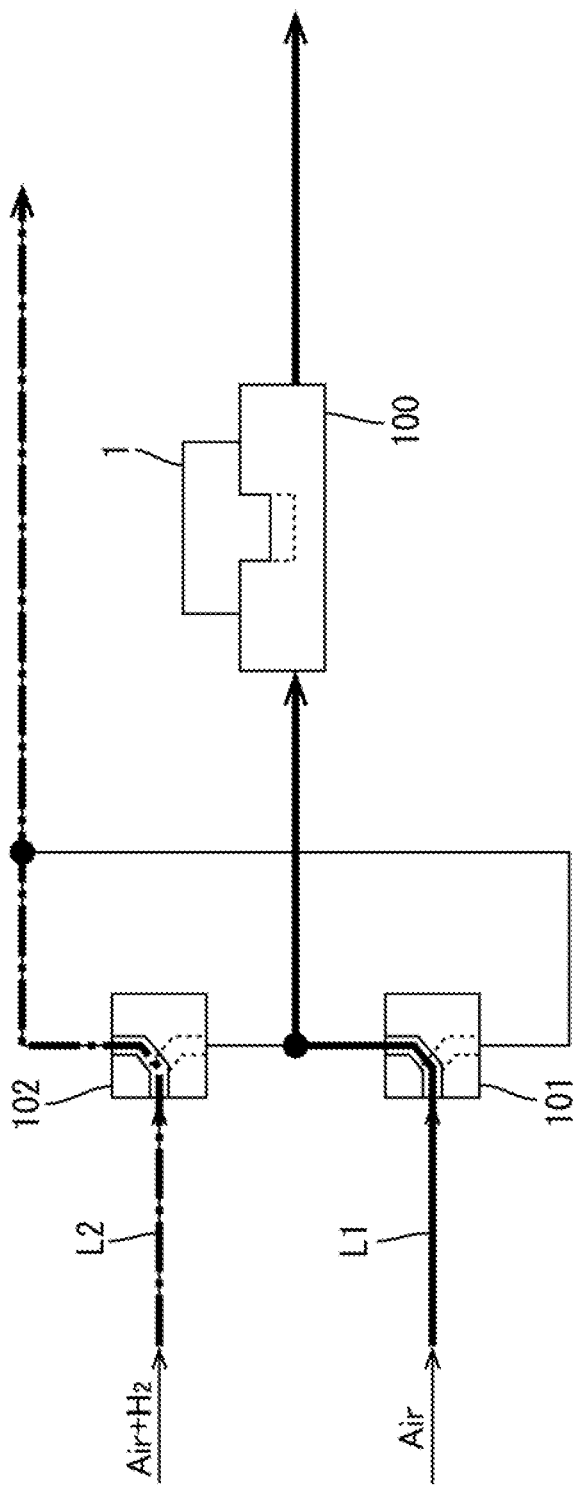
FIG. 6 is an explanatory diagram schematically showing the configuration (before changeover) of a detection target gas response test.
Figure 7:
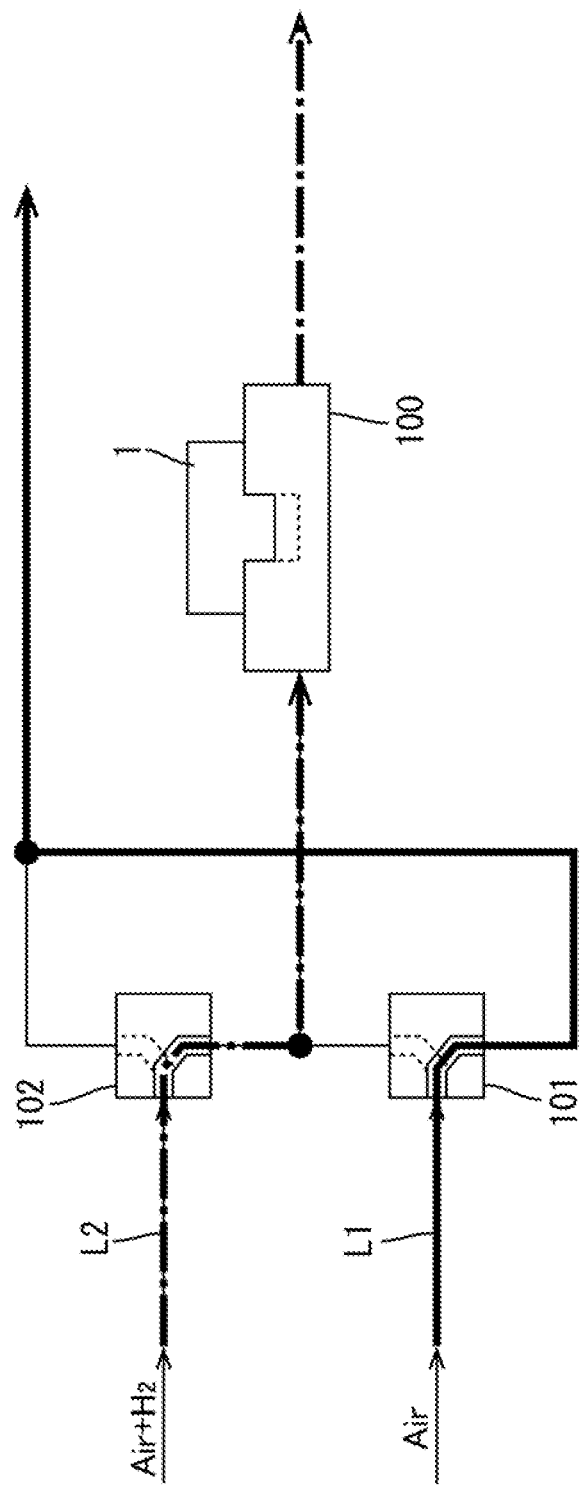
FIG. 7 is an explanatory diagram schematically showing the configuration (after changeover) of the detection target gas response test.

FIGS. 6 and 7 are explanatory diagrams which schematically show the configuration of the detection target gas response test. FIGS. 6 and 7 show the gas sensor 1 disposed in a predetermined measuring chamber 100, two lines L1 and L2 for supplying respective types of gases to the measuring chamber 100, and two three-way valves (solenoid valves) 101 and 102 for switching the type of gas to be supplied to the measuring chamber 100. The line L1 supplies air having a concentration of the detection target gas (herein, hydrogen gas) of 0 vol %. By contrast, the line L2 supplies air containing the detection target gas (hydrogen gas) at a concentration of 2 vol %. FIG. 6 shows a state in which air not containing the detection target gas (hydrogen gas at a concentration of 0 vol %) is supplied to the measurement chamber 100 through the line L1. FIG. 7 shows a state in which air having a detection target gas (hydrogen gas) concentration of 2 vol % is supplied to the measurement chamber 100 through the line L2. Air supplied to the measuring chamber 100 is discharged as appropriate.

The detection target gas response test measures the response time Y (sec) for the detection target gas at the time when the three-way valves 101 and 102 are operated for switching from the state in which predetermined air (detection target gas concentration: 0 vol %) is supplied to the measuring chamber 100 through the line L1 as shown in FIG. 6 to the state in which predetermined air containing the detection target gas (detection target gas concentration: 2 vol %) is supplied to the measuring chamber 100 through the line L2 as shown in FIG. 7.

During the detection target gas response test, the water vapor concentration (absolute humidity) in the measuring chamber 100 is held at 2 vol %. The gas flow rates of the lines L1 and L2 are set at 5 L/min.

Figure 8:
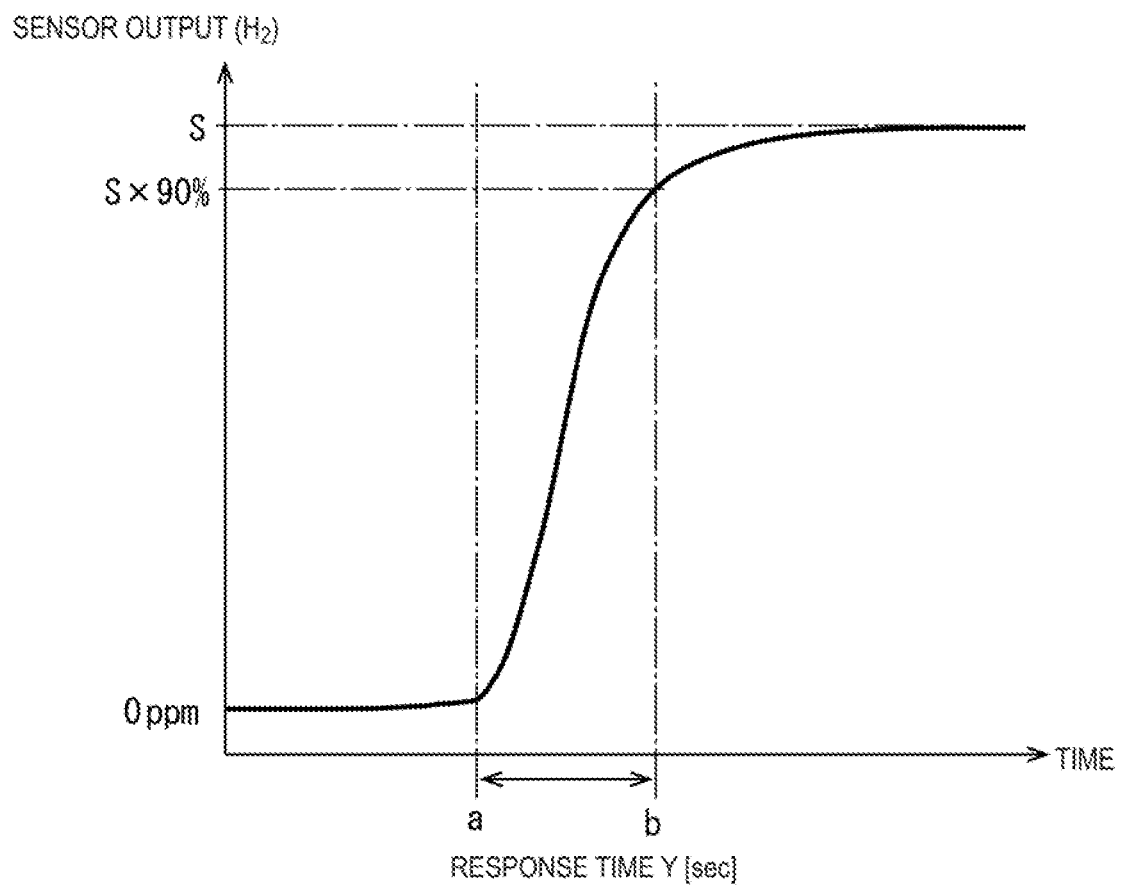
FIG. 8 is a graph showing the results of the detection target gas response test.

FIG. 8 is a graph showing the results of the detection target gas response test. The vertical axis of FIG. 8 indicates the sensor output ($H_2$ ppm) of the gas sensor 1, and the horizontal axis indicates time (sec). The following description relates to the case where the detection target gas is hydrogen gas. As shown in FIG. 8, the response time Y (sec) is obtained from a start point a (sec) and an end point b (sec) defined below. The start point a (sec) is the time at which the gas sensor 1 begins to respond to hydrogen gas (detection target gas) (the time at which the sensor output begins to increase) upon switchover from the line L1 to the line L2 with the three-way valves 101 and 102. In a state in which, after switchover with the three-way valves 101 and 102, predetermined air (hydrogen concentration: 2 vol %) is supplied to the measuring chamber 100 through the line L2, the sensor output of the gas sensor 1 assumes a stable value (stable point S). The end point b (sec) is a time when the sensor output reaches 90% of the stable value (S×0.9). A value obtained by subtracting the start point a (sec) from the end point b (sec) is the response time Y (sec) of the gas sensor 1 for hydrogen gas (detection target gas).

Figure 9:
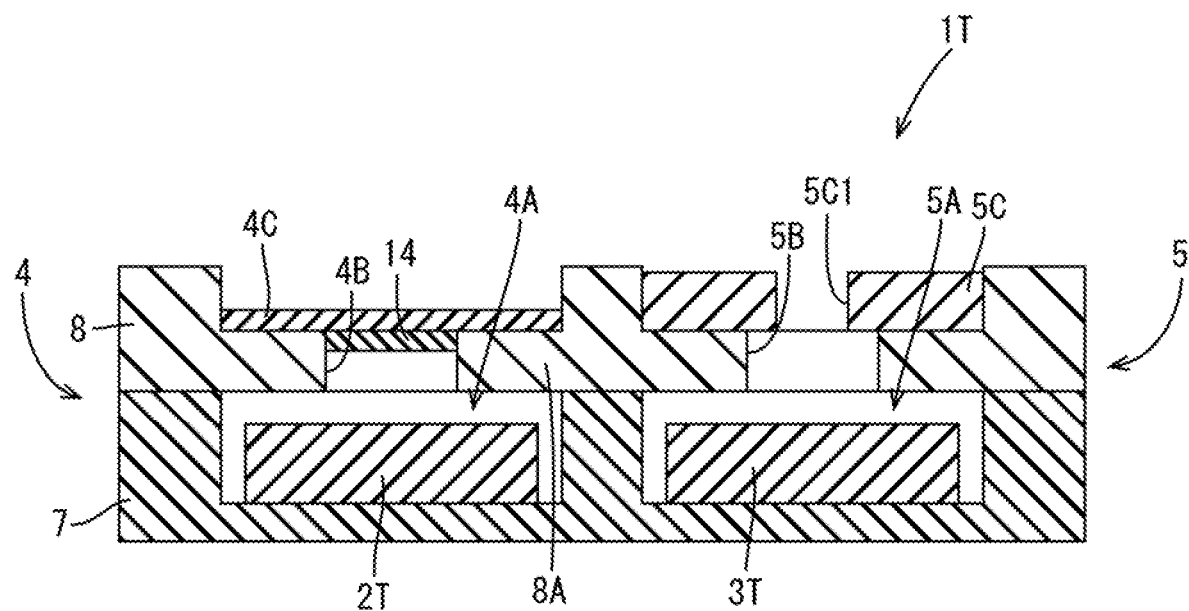
FIG. 9 is a fragmentary enlarged sectional view schematically showing the structures of the first storage portion and the second storage portion of a gas sensor for a humidity transition test.

Next, the humidity transition test will be described with reference to FIGS. 9 to 11. In the humidity transition test, the difference in water vapor concentration between the first internal space 4A and the second internal space 5A is measured by suddenly changing the concentration of water vapor contained in the detection subject atmosphere from 2 vol % to 18 vol % at a temperature of 60° C. in a state in which the detection subject atmosphere does not contain the detection target gas (e.g., does not contain hydrogen gas). FIG. 9 is a fragmentary enlarged sectional view schematically showing the structures of the first storage portion 4 and the second storage portion 5 of a gas sensor 1T for the humidity transition test. The humidity transition test uses the gas sensor 1T having temperature-humidity sensors 2T and 3T in place of the first gas detection element 2 and the second gas detection element 3, respectively, of the above-mentioned gas sensor 1. The temperature-humidity sensors 2T and 3T are composed of a known capacitance-type semiconductor element for detecting relative humidity, etc. The gas sensor 1T is identical with the gas sensor 1 in basic structure except for the temperature-humidity sensors 2T and 3T. In FIG. 9, structural members of the gas sensor 1T identical with those of the gas sensor 1 are denoted by the same reference numerals as those of the gas sensor 1, and a repeated description thereof is omitted.

Similar to the gas sensor 1 for the detection target gas response test mentioned above, the gas sensor 1T for the humidity transition test is configured such that the opening area of the first opening 4B on the reference side and the opening area of the second opening 5B on the detection side are set to 3.4 mm$^2$ (1.7 mm×2.0 mm). Further, the volume of the first internal space 4A on the reference side and the volume of the second internal space 5A on the detection side are set to 8.1 mm$^3$.

Figure 10:
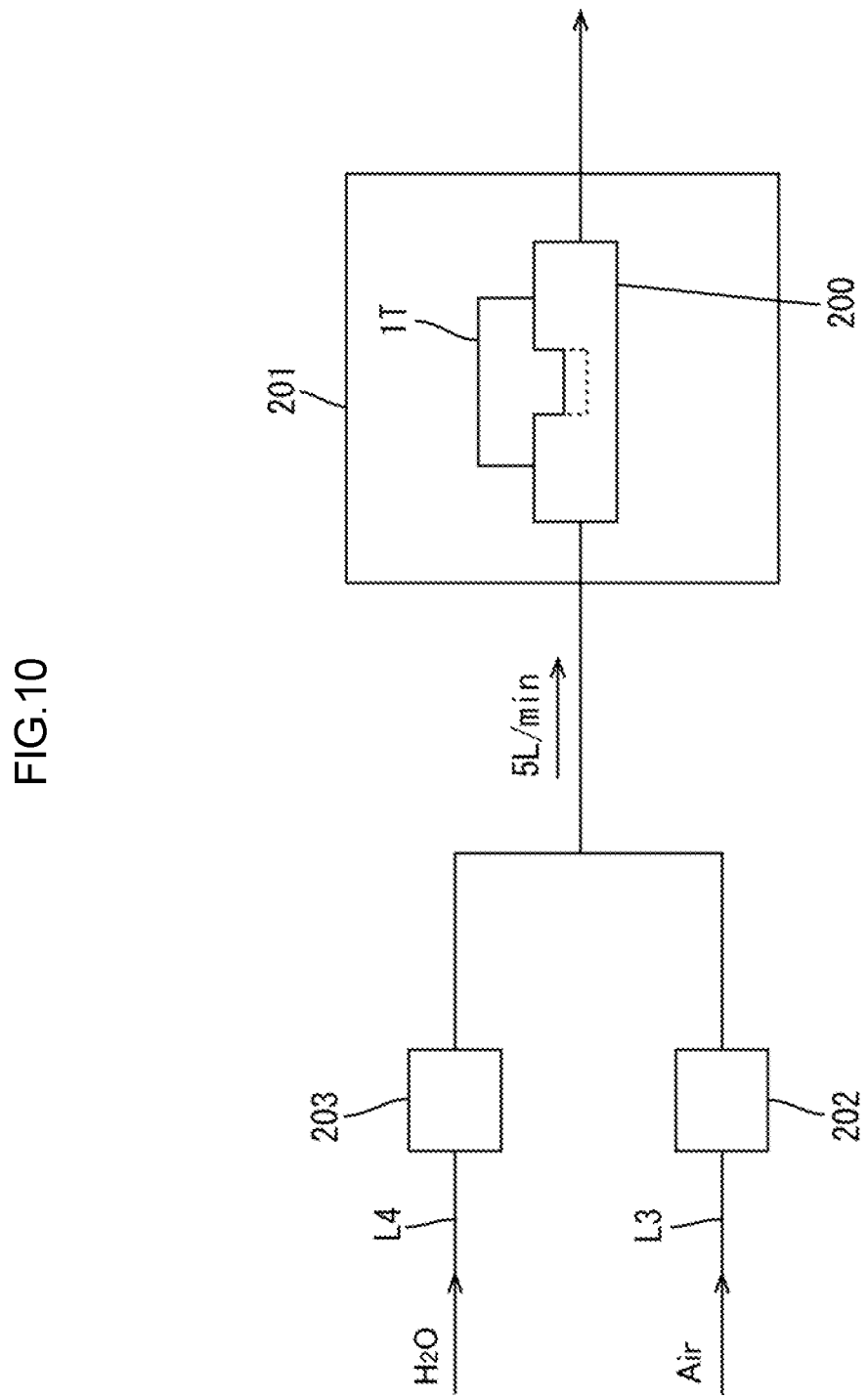
FIG. 10 is an explanatory diagram schematically showing the conditions of the humidity transition test.

FIG. 10 is an explanatory diagram which schematically shows the configuration of the humidity transition test. FIG. 10 shows the gas sensor 1T for the humidity transition test disposed in a predetermined measuring chamber 200, a thermostatic chamber 201 for accommodating the gas sensor 1T for the humidity transition test disposed in the measuring chamber 200, a line L3 for supplying air to the measuring chamber 200, a line L4 for supplying air containing water vapor to the measuring chamber 200, a mass flow controller 202 provided in the line L3 and adapted to control the flow rate of air supplied through the line L3, and a mass flow controller 203 provided in the line L4 and adapted to control the flow rate of air containing water vapor supplied through the line L4.

The temperature in the thermostatic chamber 201 is set at 60° C. The line L3 and the line L4 are connected to each other at a position located downstream of the mass flow controllers 202 and 203. Air which is supplied through the line L3 and whose flow rate has been controlled by the mass flow controller 202 and air containing water vapor which is supplied through the line 4 and whose flow rate has been controlled by the mass flow controller 203 are joined, and resultant air mixture is supplied to the measuring chamber 200. The concentration of water vapor contained in air to be supplied to the measuring chamber 200 can be adjusted by appropriately controlling the flow rates in the lines L3 and L4 by operating the mass flow controllers 202 and 203. In the humidity transition test, the detection target gas (hydrogen gas) is not supplied to the measuring chamber 200; thus, the detection target gas concentration (hydrogen concentration) is 0 vol %. The flow rate of air supplied to the measuring chamber 200 is set to a fixed value of 5 L/min. Air supplied to the measuring chamber 200 is discharged as appropriate.

In the humidity transition test, first, air containing water vapor is supplied to the measuring chamber 200 accommodated in the thermostatic chamber 201. The measuring chamber 200 is maintained at 60° C. so as to stabilize the water vapor concentration (absolute humidity) in the measuring chamber 200 at 2 vol %. Next, the flow rate of air containing water vapor supplied through the line L4 is changed by operating the mass flow controller 203, so as to supply air having a water vapor concentration (absolute humidity) of 18 vol % to the measuring chamber 200. In the humidity transition test, the difference in water vapor concentration is measured between the first internal space 4A and the second internal space 5A of the gas sensor 1T upon a sudden change in water vapor concentration from 2 vol % to 18 vol %.

Figure 11:
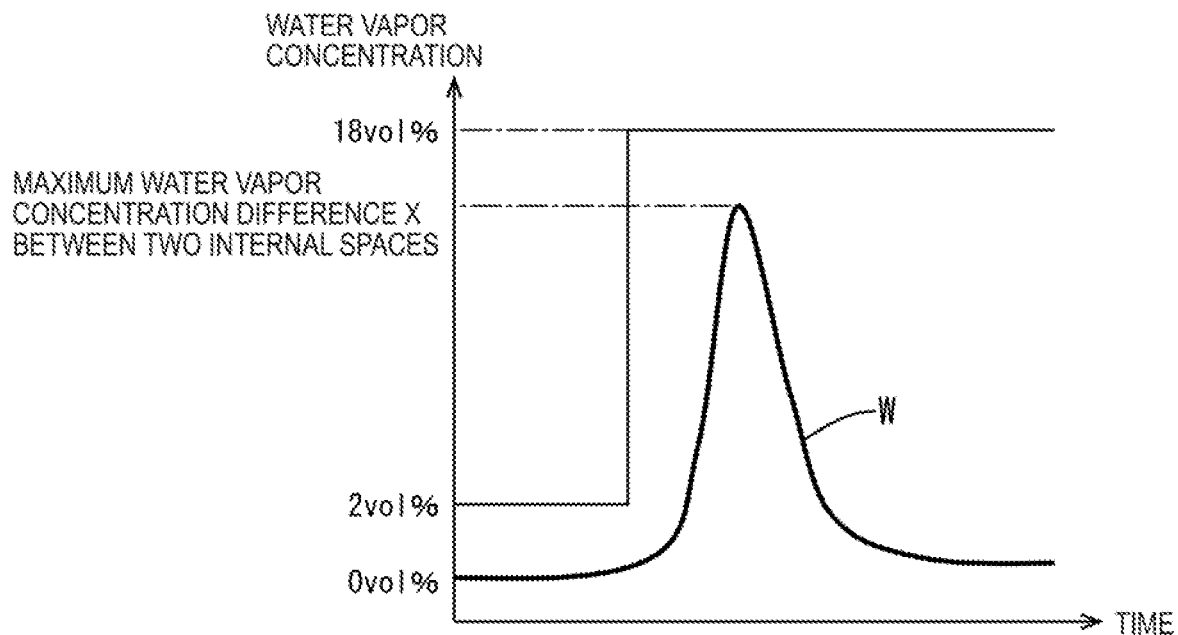
FIG. 11 is a graph showing the results of the humidity transition test.

FIG. 11 is a graph showing the results of the humidity transition test. The vertical axis of FIG. 11 indicates the water vapor concentration (vol %) of the detection subject atmosphere, and the horizontal axis indicates time. FIG. 11 shows the water vapor concentration (vol %) of air (i.e., the detection subject atmosphere) supplied to the measuring chamber 200. FIG. 11 also shows the difference in water vapor concentration between two internal spaces (the first internal space 4A and the second internal space 5A) by a curved line W. FIG. 11 also shows a maximum water vapor concentration difference X between the two internal spaces (the first internal space 4A and the second internal space 5A). As mentioned above, in the humidity transition test, the water vapor concentration difference between the first internal space 4A and the second internal space is measured upon a sudden change in water vapor concentration from 2 vol % to 18 vol % of air (i.e., the detection subject atmosphere) supplied to the measuring chamber 200, at a temperature of 60° C. Based on the results of the measurement, the maximum water vapor concentration difference X (vol %) is obtained.

Verification of the Influence of the Thickness of the Second Membrane

Figure 12:
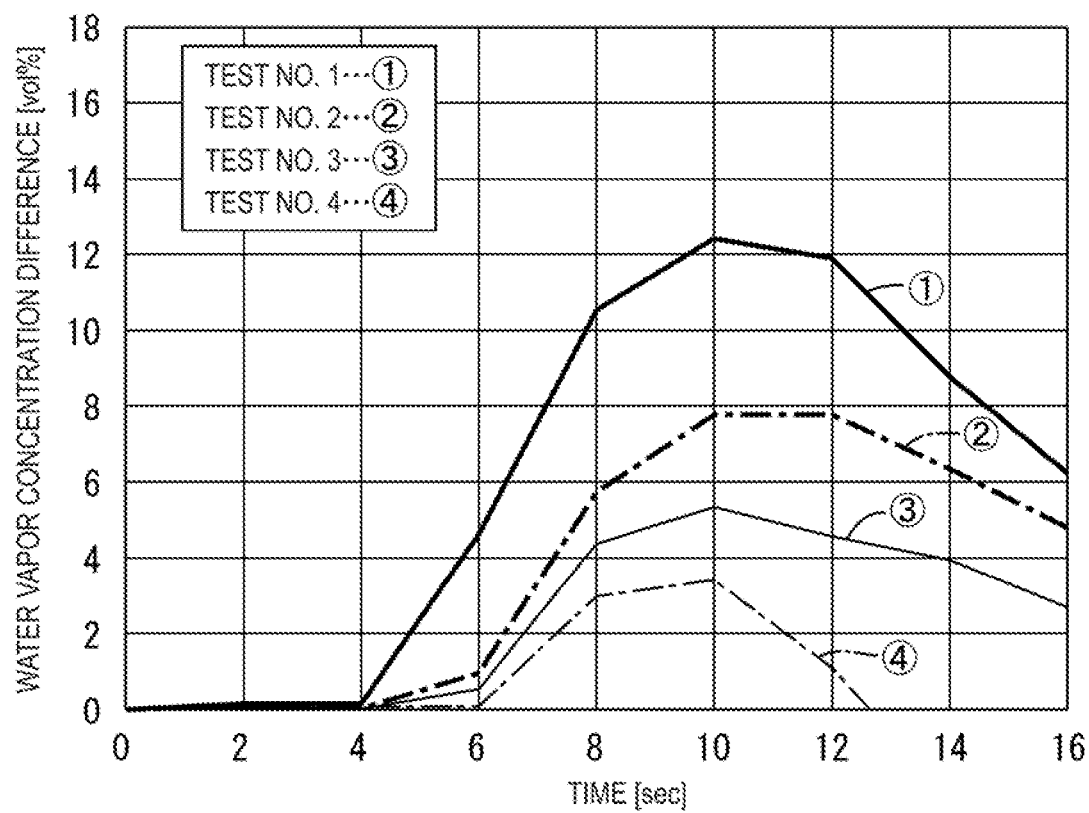
FIG. 12 is a graph showing the results of the humidity transition test with respect to test Nos. 1 to 4.
Figure 13:
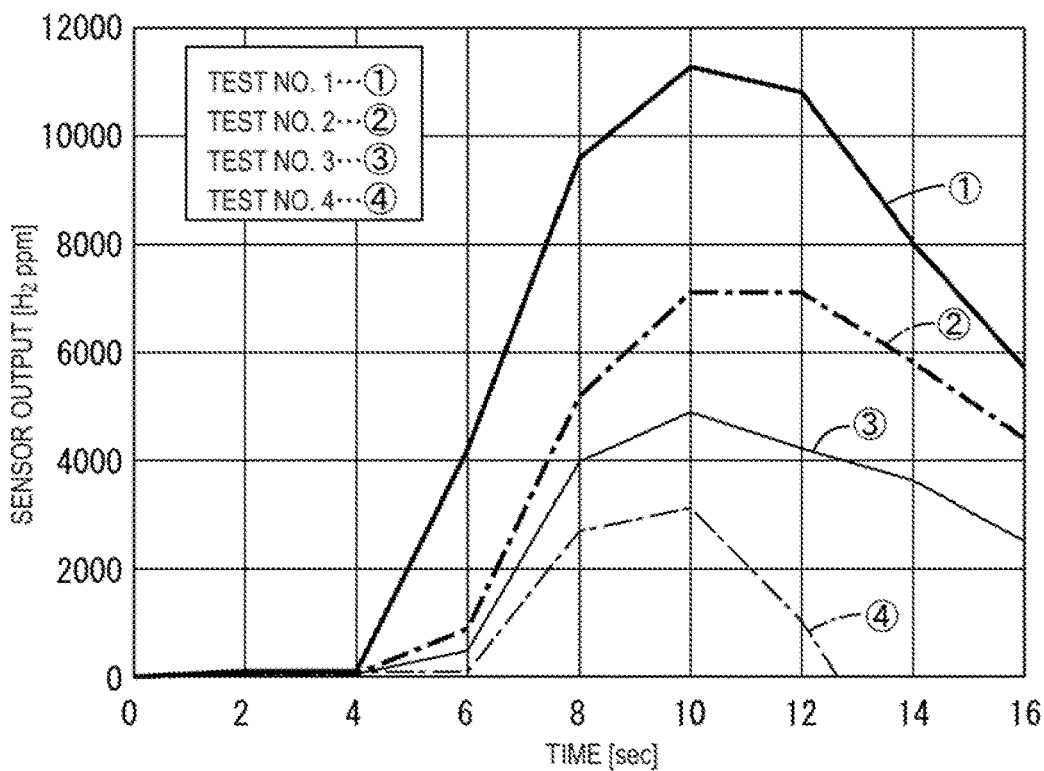
FIG. 13 is a graph showing the results (converted to hydrogen concentration) of the humidity transition test with respect to test Nos. 1 to 4.

Next, the influence of the thickness of the second membrane of the gas sensor 1 was verified with respect to the difference in water vapor concentration between the first internal space 4A and the second internal space 5A. Specifically, the humidity transition test was conducted on the gas sensors 1T for test use having the first membranes and the second membranes prepared under the conditions of test Nos. 1 to 4, respectively, shown in Table 1. FIGS. 12 and 13 show the results of the humidity transition test.

TABLE 1

| TEST NO. | FIRST MEMBRANE (REFERENCE SIDE) | | SECOND MEMBRANE (DETECTION SIDE) | | RESPONSE TIME Y (sec) |
|---|---|---|---|---|---|
| | TYPE | THICKNESS (μm) | TYPE | THICKNESS (μm) | |
| 1 | TYPE A (WITH CATALYST LAYER) | 15 | TYPE A | 15 | 2.3 |
| 2 | TYPE A (WITH CATALYST LAYER) | 15 | TYPE A | 30 | 2.4 |
| 3 | TYPE A (WITH CATALYST LAYER) | 15 | TYPE A | 60 | 2.3 |
| 4 | TYPE A (WITH CATALYST LAYER) | 15 | TYPE A | 120 | 2.4 |

"Type" appearing in Table 1 shows the type of material used to form the first membrane and the second membrane. "Type A" appearing in Table 1 is a perfluorosulfonic acid membrane (commercial product) including an extensible Teflon® framework and a sulfonate group. "Type A (with catalyst layer)" is the perfluorosulfonic acid membrane on which a catalyst layer is formed (commercial product). The type of material used to form the first membrane and the second membrane is also designated similarly in other tables as in Table 1.

In the gas sensors 1 having the first membranes and the second membranes prepared under the conditions of test Nos. 1 to 4, respectively, the sizes of communication holes formed in the respective second membranes were determined such that the response time Y obtained by conducting the detection target gas response test using hydrogen as the detection target gas became 3 seconds or less. Table 1 shows the results of measurement of the response time Y of test Nos. 1 to 4.

FIGS. 12 and 13 are graphs showing the results of the humidity transition test in test Nos. 1 to 4. The vertical axis of FIG. 12 indicates the difference in water vapor concentration (vol %) between the first internal space 4A and the second internal space 5A, and the horizontal axis indicates time (sec). The vertical axis of FIG. 13 indicates the sensor output ($H_2$ ppm) indicative of the difference in water vapor concentration between the first internal space 4A and the second internal space 5A converted to hydrogen concentration, and the horizontal axis indicates time (sec). As shown in FIGS. 12 and 13, when the thickness of the second membrane on the detection side is greater than that of the first membrane on the reference side, as the difference in thickness between the first and second membranes increases, the water vapor concentration difference is reduced between the first internal space 4A on the reference side and the second internal space 5A on the detection side in the humidity transition test.

Verification of the Influence of the Material of the First Membrane

Figure 14:
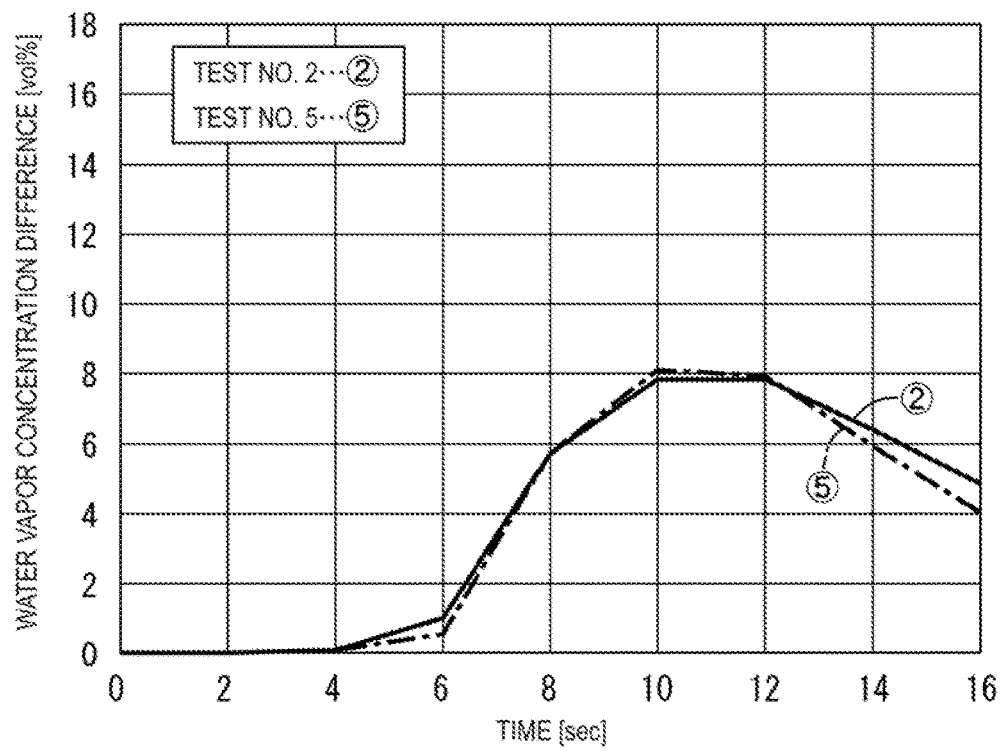
FIG. 14 is a graph showing the results of the humidity transition test with respect to test Nos. 2 and 5.
Figure 15:
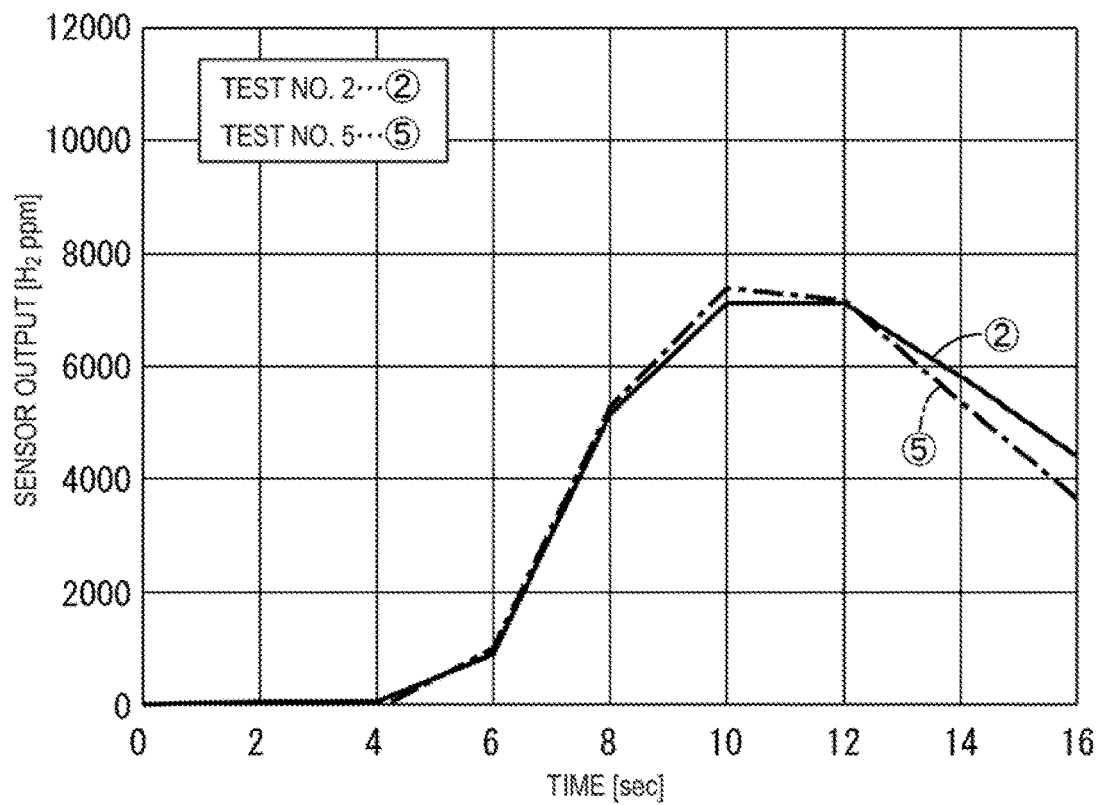
FIG. 15 is a graph showing the results (converted to hydrogen concentration) of the humidity transition test with respect to test Nos. 2 and 5.

Next, the influence of the material of the first membrane of the gas sensor 1 was verified with respect to the difference in water vapor concentration between the first internal space 4A and the second internal space 5A. Specifically, the humidity transition test was conducted on the gas sensors 1T for test use having the first membranes and the second membranes prepared under the conditions of test Nos. 2 and 5, respectively, shown in Table 2. Notably, test No. 2 is the same as the above-mentioned test No. 2. FIGS. 14 and 15 show the results of the humidity transition test.

TABLE 2

| TEST NO. | FIRST MEMBRANE (REFERENCE SIDE) | | SECOND MEMBRANE (DETECTION SIDE) | | RESPONSE TIME Y (sec) |
|---|---|---|---|---|---|
| | TYPE | THICKNESS (μm) | TYPE | THICKNESS (μm) | |
| 2 | TYPE A (WITH CATALYST LAYER) | 15 | TYPE A | 30 | 2.4 |
| 5 | TYPE A (WITH CATALYST LAYER) | 15 | TYPE B | 30 | 2.4 |

"Type B" appearing in Table 2 is a perfluorosulfonic acid membrane produced by DuPont (Nafion®).

In the gas sensors 1 having the first membranes and the second membranes prepared under the conditions of test Nos. 2 and 5, respectively, the sizes of communication holes formed in the respective second membranes were determined such that the response time Y obtained by conducting the detection target gas response test using hydrogen gas as the detection target gas became 3 seconds or less. Table 2 shows the results of measurement of the response time Y of test Nos. 2 and 5.

FIGS. 14 and 15 are graphs showing the results of the humidity transition test in test Nos. 2 and 5. The vertical axis of FIG. 14 indicates the difference in water vapor concentration (vol %) between the first internal space 4A and the second internal space 5A, and the horizontal axis indicates time (sec). The vertical axis of FIG. 15 indicates the sensor output ($H_2$ ppm) indicative of the difference in water vapor concentration between the first internal space 4A and the second internal space 5A converted to hydrogen concentration, and the horizontal axis indicates time (sec). In test No. 2 and test No. 5, the first and second membranes had the same thickness. Test No. 2 and test No. 5 differ with respect to the type of material used to form the second membrane on the detection side. However, since each of the second membrane 5C of type A of test No. 2 and the second membrane 5C of type B of test No. 5 is a type of fluororesin ion exchange membrane, as shown in FIGS. 14 and 15, test No. 2 and test No. 5 show almost the same results in the humidity transition test.

Verification of the Influence of the Thickness of the First Membrane

Figure 16:
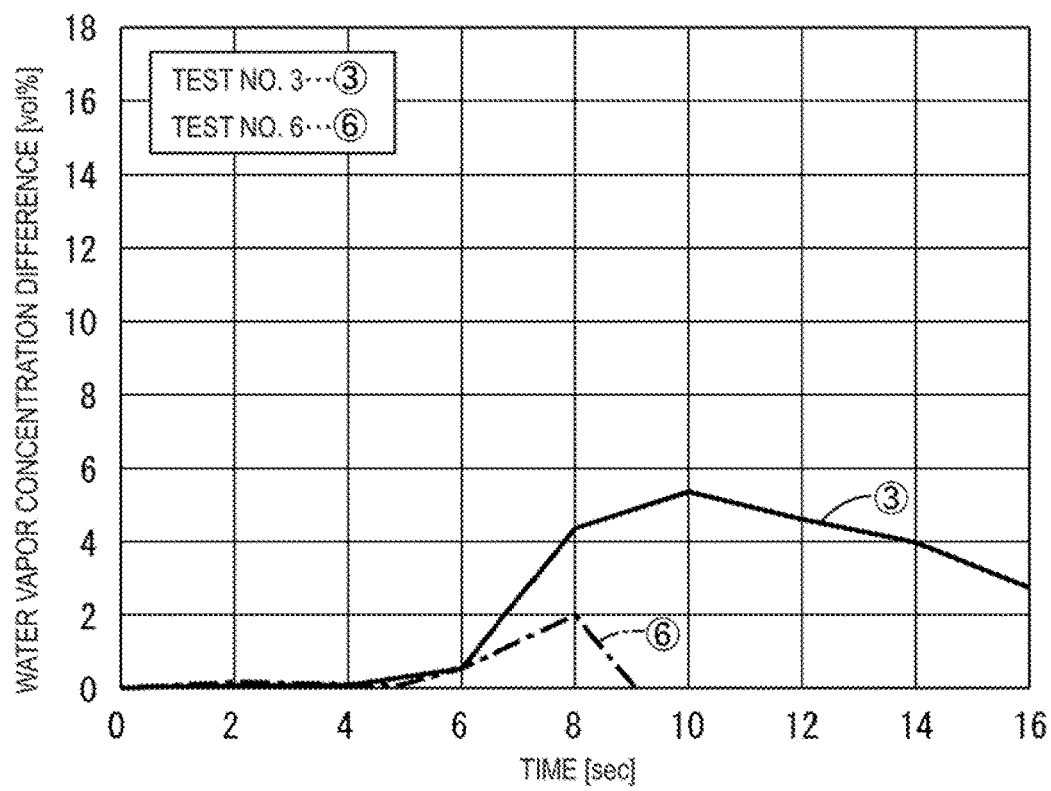
FIG. 16 is a graph showing the results of the humidity transition test with respect to test Nos. 3 and 6.
Figure 17:
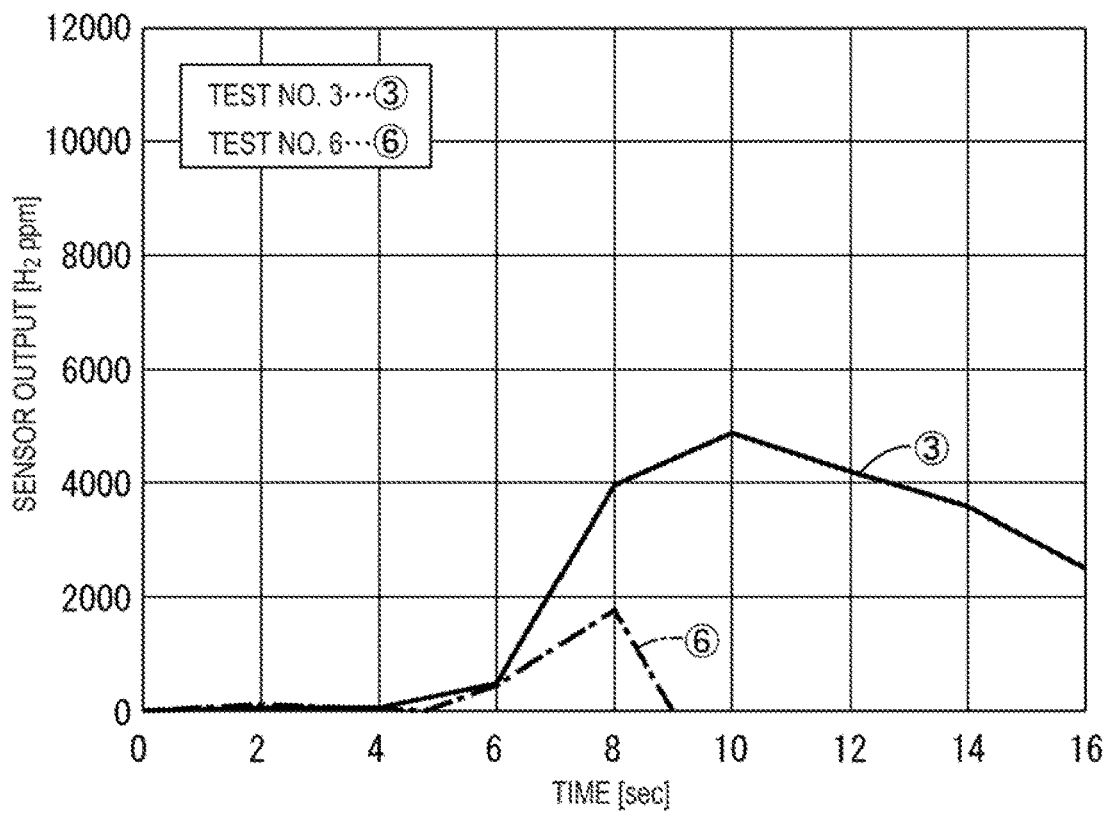
FIG. 17 is a graph showing the results (converted to hydrogen concentration) of the humidity transition test with respect to test Nos. 3 and 6.

Next, the influence of the thickness of the first membrane 4C of the gas sensor 1 was verified with respect to the difference in water vapor concentration between the first internal space 4A and the second internal space 5A. Specifically, the humidity transition test was conducted on the gas sensors 1T for test use having the first membranes and the second membranes prepared under the conditions of test Nos. 3 and 6, respectively, shown in Table 3. Notably, test No. 3 is the same as the above-mentioned test No. 3. FIGS. 16 and 17 show the results of the humidity transition test.

TABLE 3

| TEST NO. | FIRST MEMBRANE (REFERENCE SIDE) | | SECOND MEMBRANE (DETECTION SIDE) | | RESPONSE TIME Y (sec) |
|---|---|---|---|---|---|
| | TYPE | THICKNESS (μm) | TYPE | THICKNESS (μm) | |
| 3 | TYPE A (WITH CATALYST LAYER) | 15 | TYPE A | 60 | 2.3 |
| 6 | TYPE A (WITH CATALYST LAYER) | 7.5 | TYPE A | 60 | 2.3 |

In the gas sensors 1 having the first membranes and the second membranes prepared under the conditions of test Nos. 3 and 6, respectively, the sizes of communication holes formed in the respective second membranes were determined such that the response time Y obtained by conducting the detection target gas response test using hydrogen gas as the detection target gas became 3 seconds or less. Table 3 shows the results of measurement of the response time Y of test Nos. 3 and 6.

FIGS. 16 and 17 are graphs showing the results of the humidity transition test in test Nos. 3 and 6. The vertical axis of FIG. 16 indicates the difference in water vapor concentration (vol %) between the first internal space 4A and the second internal space 5A, and the horizontal axis indicates time (sec). The vertical axis of FIG. 17 indicates the sensor output ($H_2$ ppm) indicative of the difference in water vapor concentration between the first internal space 4A and the second internal space 5A converted to hydrogen concentration, and the horizontal axis indicates time (sec). As shown in FIGS. 16 and 17, when the second membranes on the detection side have the same thickness, a reduction in the thickness of the first membrane on the reference side reduces the water vapor concentration difference between the first internal space 4A on the reference side and the second internal space 5A on the detection side in the humidity transition test. This is because a reduction in the thickness of the first membrane reduces the time required for the movement of water vapor (water molecules) through the first membrane.

Figure 18:
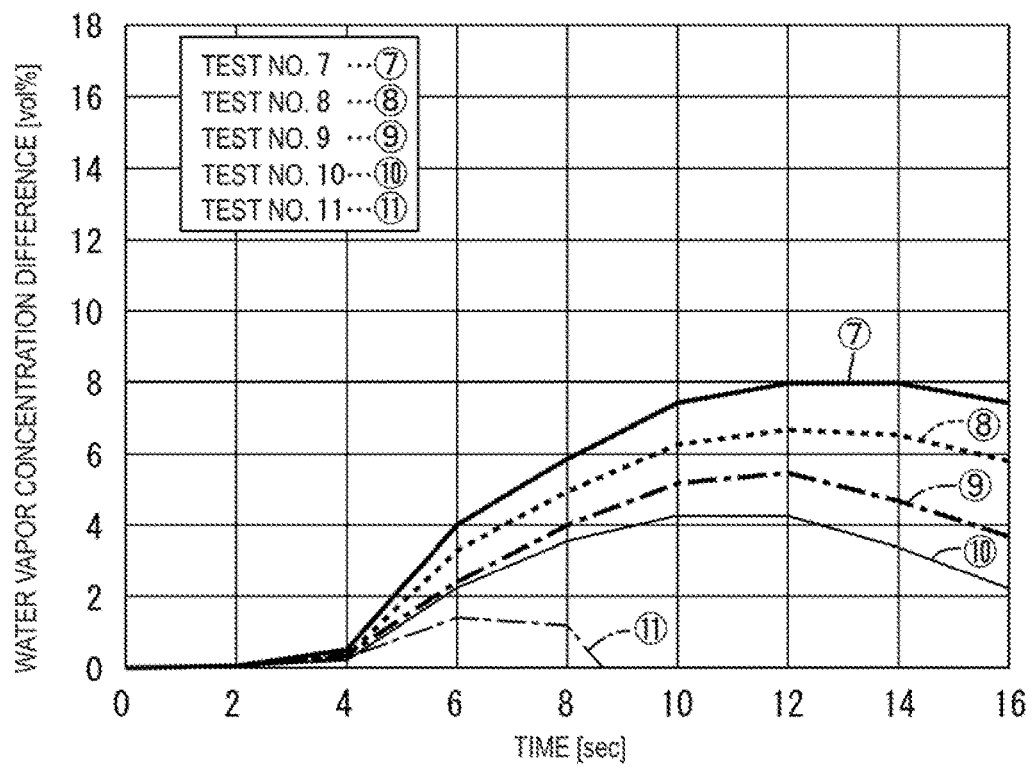
FIG. 18 is a graph showing the results of the humidity transition test with respect to test Nos. 7 to 11.
Figure 19:
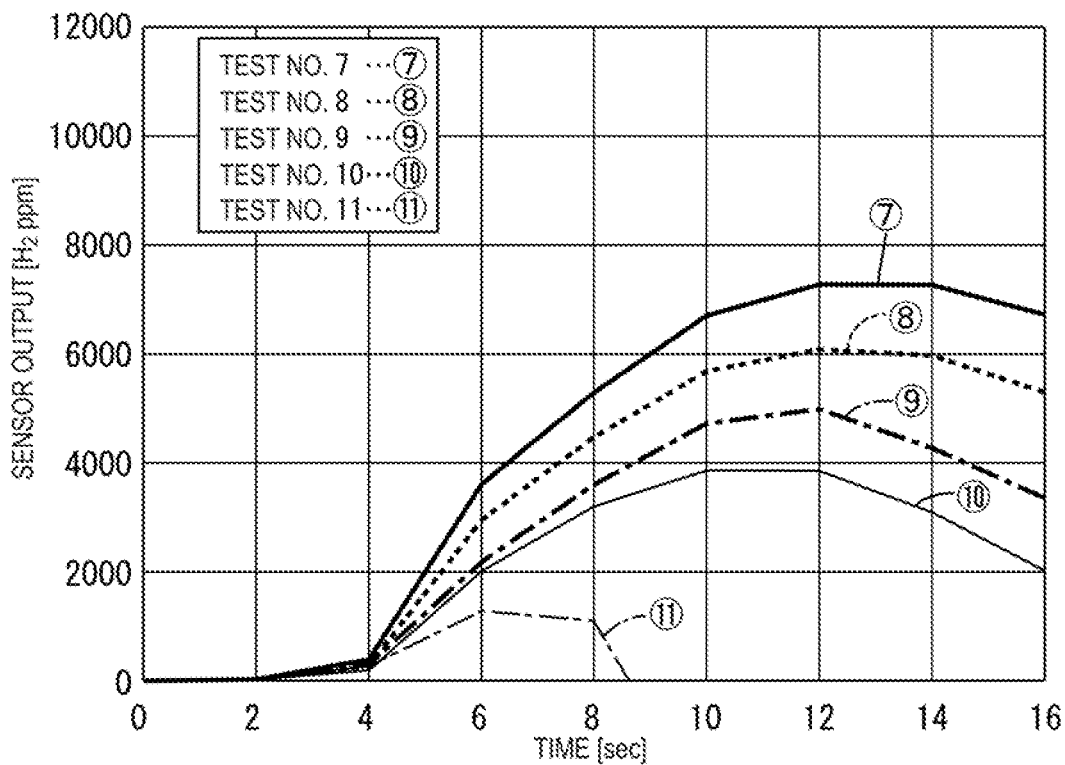
FIG. 19 is a graph showing the results (converted to hydrogen concentration) of the humidity transition test with respect to test Nos. 7 to 11.

Verification of the Influence of the Diameter of the Communication Hole of the Second Membrane Next, the influence of the size of communication hole (communication hole diameter) of the second membrane of the gas sensor 1 was verified with respect to the difference in water vapor concentration between the first internal space 4A and the second internal space 5A. Specifically, the humidity transition test was conducted on the gas sensors 1T for test use having the first membranes and the second membranes prepared under the conditions of test Nos. 7 to 11, respectively, shown in Table 4. FIGS. 18 and 19 show the results of the humidity transition test.

Figure 20:
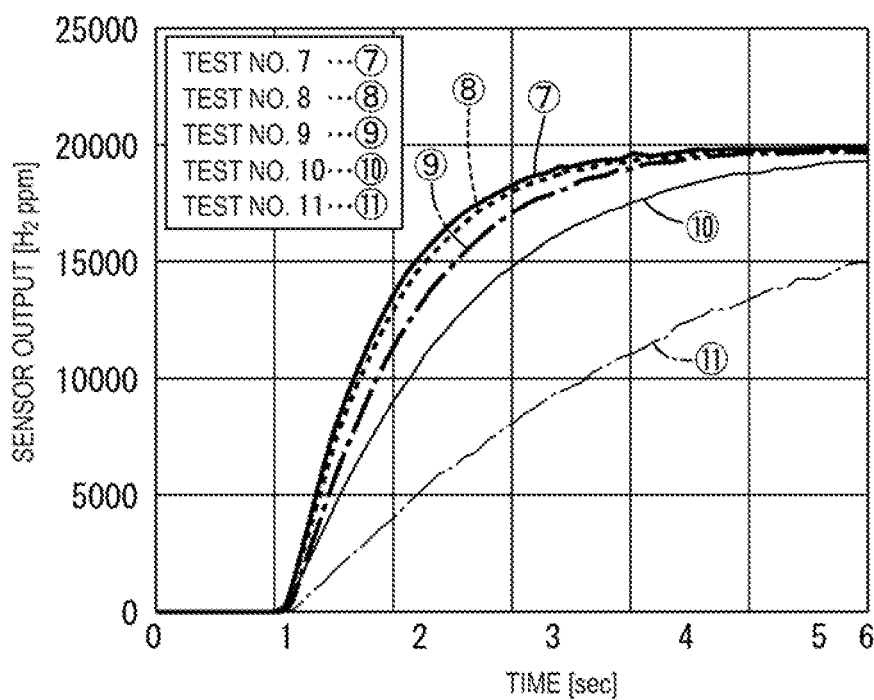
FIG. 20 is a graph showing the results of a hydrogen gas response test with respect to test Nos. 7 to 11.

The detection target gas response test (hydrogen gas response test) using hydrogen gas as a detection target gas was conducted on the gas sensors 1 having the first membranes and the second membranes prepared under the conditions of test Nos. 7 to 11, respectively, thereby measuring the response time Y. Table 5 and FIG. 20 show the results of measurement of the response time Y of test Nos. 7 to 11.

TABLE 4

| TEST NO. | FIRST MEMBRANE (REFERENCE SIDE) | | SECOND MEMBRANE (DETECTION SIDE) | | |
|---|---|---|---|---|---|
| | TYPE | THICKNESS (μm) | TYPE | THICKNESS (μm) | COMMUNICATION HOLE DIAMETER (mm) |
| 7 | TYPE A (WITH CATALYST LAYER) | 15 | TYPE A | 60 | 0.4 |
| 8 | TYPE A (WITH CATALYST LAYER) | 15 | TYPE A | 60 | 0.3 |
| 9 | TYPE A (WITH CATALYST LAYER) | 15 | TYPE A | 60 | 0.2 |
| 10 | TYPE A (WITH CATALYST LAYER) | 15 | TYPE A | 60 | 0.1 |
| 11 | TYPE A (WITH CATALYST LAYER) | 15 | TYPE A | 60 | 0.01 |

TABLE 5

| TEST NO. | COMMUNICATION HOLE DIAMETER (mm) | RESPONSE TIME Y (sec) | WATER VAPOR CONCENTRATION DIFFERENCE X (volume %) |
|---|---|---|---|
| 7 | 0.4 | 1.3 | 8.0 |
| 8 | 0.3 | 1.4 | 6.7 |
| 9 | 0.2 | 2.3 | 5.5 |
| 10 | 0.1 | 3.3 | 4.3 |
| 11 | 0.01 | 7.5 | 1.4 |

FIGS. 18 and 19 are graphs showing the results of the humidity transition test in test Nos. 7 to 11. The vertical axis of FIG. 18 indicates the difference in water vapor concentration (vol %) between the first internal space 4A and the second internal space 5A, and the horizontal axis indicates time (sec). The vertical axis of FIG. 19 indicates the sensor output ($H_2$ ppm) indicative of the difference in water vapor concentration between the first internal space 4A and the second internal space 5A converted to hydrogen concentration, and the horizontal axis indicates time (sec). FIG. 20 is a graph showing the results of the hydrogen gas response test in test Nos. 7 to 11. The vertical axis of FIG. 20 indicates the sensor output ($H_2$ ppm) of the gas sensor 1, and the horizontal axis indicates time (sec).

As shown in Table 5 and FIGS. 19 and 20, the following has been verified: the greater the size of communication hole (communication hole diameter) of the second membrane on the detection side, the greater the ease of hydrogen gas entering the second internal space 5A on the detection side, and the shorter the response time Y for hydrogen gas. However, the greater the size of communication hole, the greater the difference in water vapor concentration (maximum water vapor concentration difference X) between the first internal space 4A on the reference side and the second internal space 5A on the detection side in the humidity transition test. That is, it is understood that the response time Y for hydrogen gas and the maximum water vapor concentration difference X are in a so-called trade-off relation.

Other Embodiments

The present invention is not limited to the embodiment described above with reference to the drawings. For example, the following embodiments are also encompassed in the technical scope of the present invention.

(1) In the gas sensor 1 of the above first embodiment, the communication hole 5C1 formed in the second membrane 5C has a circular shape in a plan view. However, no particular limitation is imposed on the shape of the communication hole so long as the purpose of the present invention is not impaired. Also, no particular limitation is imposed on the number of communication holes formed in the second membrane 5C, so long as the purpose of the present invention is not impaired. For example, the number of communication holes may be two or more.

(2) In the gas sensor 1 of the above first embodiment, the catalyst layer 14 is formed on the first membrane 4C. However, the first membrane not having the catalyst layer 14 may be used in other embodiments.

(3) In the above first embodiment, the difference in water vapor concentration (maximum water vapor concentration difference X) between the first internal space 4A and the second internal space 5A is set to 7 vol % or less. However, in other embodiments, the maximum water vapor concentration difference X may be optionally set to 6.5 vol % or less, further, to 6 vol % or less. When the maximum water vapor concentration difference X is 6.5 vol % or less, since the difference in water vapor concentration between the first internal space and the second internal space becomes 5,900 ppm or less converted to hydrogen concentration, the detection target gas concentration can be measured more accurately. Also, when the maximum water vapor concentration difference X is 6 vol % or less, since the difference in water vapor concentration between the first internal space and the second internal space becomes 5,400 ppm or less converted to hydrogen concentration, the detection target gas concentration can be measured far more accurately.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. JP 2019-015445 filed Jan. 31, 2019, incorporated herein by reference in its entirety.

What is claimed is:

1. A gas sensor comprising:
   paired first and second thermal conduction type gas detection elements;
   a first storage portion having a first internal space in which the first gas detection element is disposed, and having a first opening establishing communication between the first internal space and an outside space exposed to a detection subject atmosphere;
   a second storage portion having a second internal space in which the second gas detection element is disposed, and having a second opening establishing communication between the second internal space and the outside space;
   a first membrane formed of a material allowing permeation of water vapor and substantially not allowing permeation of a detection target gas, and disposed so as to cover the first opening; and
   a calculation unit for calculating a concentration of the detection target gas contained in the detection subject atmosphere introduced into the second internal space, based on outputs from the first gas detection element and the second gas detection element, respectively;
   wherein the gas sensor further comprises a second membrane formed of the same kind of material used to form the first membrane, having a thickness larger than that of the first membrane, and disposed so as to cover the second opening;
   the second membrane having a communication hole extending therethrough in a thickness direction for establishing communication between the outside space and the second internal space; and
   the gas sensor having a response time of 3 seconds or less for detecting the concentration of the detection target gas when the concentration of the detection target gas contained in the detection subject atmosphere is suddenly changed from 0 vol % to 2 vol % at a temperature of 25° C. in a state in which the detection subject atmosphere has a water vapor concentration of 2 vol %, and a water vapor concentration difference of 7 vol % or less results between the first internal space and the second internal space when the concentration of water vapor contained in the detection subject atmosphere is suddenly changed from 2 vol % to 18 vol % at a temperature of 60° C. in a state in which the detection subject atmosphere does not contain the detection target gas.

2. The gas sensor as claimed in claim 1, wherein the detection target gas is hydrogen, and the water vapor concentration difference between the first internal space and the second internal space is 6,300 ppm or less converted to hydrogen concentration.

3. The gas sensor as claimed in claim 2, wherein the water vapor concentration difference is calculated at the value of 6,300 ppm or less converted to hydrogen concentration by the calculation unit.

* * * * *